United States Patent [19]
Barbier et al.

[11] Patent Number: 5,488,041
[45] Date of Patent: Jan. 30, 1996

[54] METHOD OF PROMOTING BONE REPAIR USING TILUDRONIC DISODIUM SALT

[75] Inventors: Alain Barbier, Saint Clement La Riviere; Frederic Lacheretz, Pignan, both of France

[73] Assignee: Sanofi, Paris, France

[21] Appl. No.: 222,240

[22] Filed: Apr. 4, 1994

[30] Foreign Application Priority Data

Apr. 5, 1993 [FR] France .................... 93 03999

[51] Int. Cl.$^6$ .................... A61K 31/66; A61K 31/675
[52] U.S. Cl. .................... 514/108; 514/89; 514/111
[58] Field of Search .................... 514/108, 89, 111

[56] References Cited

U.S. PATENT DOCUMENTS

| | | | |
|---|---|---|---|
| 4,578,376 | 3/1986 | Rosini | 514/108 |
| 4,746,654 | 5/1988 | Breliere et al. | 514/108 |
| 4,876,248 | 10/1989 | Breliere et al. | 514/108 |
| 4,922,007 | 5/1990 | Kieczykowski et al. | 562/13 |
| 5,270,365 | 12/1993 | Gertz et al. | 514/108 |

FOREIGN PATENT DOCUMENTS

| | | |
|---|---|---|
| 0186405 | 7/1986 | European Pat. Off. |
| 0325482 | 7/1989 | European Pat. Off. |
| WO86/00902 | 2/1986 | WIPO |
| WO87/03598 | 6/1987 | WIPO |

OTHER PUBLICATIONS

Storm et al, "Effect Of Intermittent Cyclical Etidronate . . . Osteoporosis"; New England Journal of Medicine vol. 322, (18) PP. 1265–1271 1990.

Primary Examiner—T. J. Criares
Attorney, Agent, or Firm—Bacon & Thomas

[57] ABSTRACT

The present invention relates to a method of promoting bone repair in human or veterinary medicine; which method comprises the administration of therapeutically effective amounts of bisphosphonic acid derivatives of formula (I):

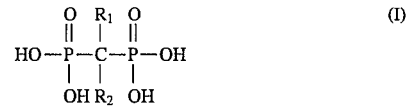

in which:

$R_1$ is a hydrogen atom, a halogen atom, a hydroxyl, an amino, a mono-$C_1$–$C_4$-alkylamino or a di-$C_1$–$C_4$-alkylamino; and $R_2$ is a halogen atom or a linear alkyl containing from 1 to 5 carbon atoms which is unsubstituted or substituted by a group selected from a chlorine atom, a hydroxyl, an amino, a mono-$C_1$–$C_4$-alkylamino, a di- $C_1$–$C_4$-alkylamino and a $C_3$–$C_7$-cycloalkylamino, or $R_2$ is a phenoxy, a phenyl, a thiol, a phenylthio, a chlorophenylthio, a pyridyl, a pyridylmethyl, a 1-pyridyl-1-hydroxymethyl, an imidazolylmethyl or a thiomorpholin-4-yl; and of their salts with pharmaceutically acceptable mineral or organic acids.

14 Claims, No Drawings

METHOD OF PROMOTING BONE REPAIR USING TILUDRONIC DISODIUM SALT

The present invention relates to a method of promoting bone repair in human or veterinary medicine; which method comprises the administration of therapeutically effective amounts of bisphosphonic acid derivatives.

The physiological process of bone repair is defined as the successive appearance of different cicatricial tissues; these are as follows, in order of appearance: cartilage, primary bone (non-organized) and then lamellar bone (organized). Each of these is only formed after the destruction of the previous one. Such a change is therefore due to a resorption, which is ensured by macrophagic cells: the chondroclasts for cartilage resorption and the osteoclasts for bone resorption. This is clearly described in Le Tissu Osseux (Bone Tissue) edited under the guidance of L. Teot, J. Vidal and J. Dossa, collection: Biologie de l'appareil locomoteur (Biology of the locomotor apparatus), Diffusion Vigot, 1989, and by H. M. Frost in The biology of fracture healing. An overview for clinicians, I and II, Clin. Orthop., 1989, 248, 283 et seq.

In the description and in the claims which follow, bisphosphonic acid derivative is understood as meaning a compound of the formula

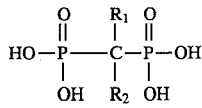

in which:

$R_1$ is a hydrogen atom, a halogen atom, a hydroxyl, an amino, a mono-C1-$C_4$alkylamino or a di-$C_1$-$C_4$-alkylamino; and $R_2$ is a halogen atom or a linear alkyl containing from 1 to 5 carbon atoms which is unsubstituted or substituted by a group selected from a chlorine atom, a hydroxyl, an amino, a mono-$C_1$-$C_4$-alkylamino, a di- $C_1$-$C_4$-alkylamino and a $C_3$-$C_7$-cycloalkylamino, or $R_2$ is a phenoxy, a phenyl, a thiol, a phenylthio, a chlorophenylthio, a pyridyl, a pyridylmethyl, a 1- pyridyl-1-hydroxymethyl, an imidazolylmethyl or a thiomorpholin-4-yl;

and its salts with pharmaceutically acceptable mineral or organic acids.

These compounds are known and have been described as drugs in the treatment of bone diseases, especially in the following patents: BE 902308, BE 865434, DE 2130794, U.S. Pat. No. 4134969, EP 162510, FR 2525223, EP 39033, U.S. Pat. No. 4578376, EP 203549, BE 822930, U.S. Pat. No. 4621077, JP 55-98193, EP 186405, EP 100718, WO 86/00902, WO 87/03598, U.S. Pat. No. 4922007, EP 304961, JP 63-150291 and EP 325482.

The following compounds may be mentioned in particular among these bisphosphonic acid derivatives:

1-hydroxyethylidenebisphosphonic acid, having the international non-proprietary name etidronic acid, and its sodium salts;

2-pyridin-2-ylethylidenebisphosphonic acid, having the international non-proprietary name piridronic acid, and its sodium salts;

dichloromethylenebisphosphonic acid, having the international non-proprietary name clodronic acid, and its sodium salts;

3-amino-1-hydroxypropylidenebisphosphonic acid, having the international non-proprietary name pamidronic acid, and its sodium salts;

4-amino-1-hydroxybutylidenebisphosphonic acid, having the international non-proprietary name alendronic acid, and its sodium salts;

6-amino-1-hydroxyhexylidenebisphosphonic acid and its salts;

phenoxymethylenebisphosphonic acid and its salts;

thiomorpholinomethylenebisphosphonic acid and its salts;

4-chlorophenyl thiomethylenebisphosphonic acid, having the non-proprietary name tiludronic acid, and its pharmaceutically acceptable salts, especially the disodium salt;

1-hydroxy-2-(pyridin-3-yl)ethylidenebisphosphonic acid, having the international non-proprietary name risedronic acid, and its sodium salts;

1-hydroxy-2-(imidazol-2-yl)ethyl-1,1-bisphosphonic acid and its salts;

(cycloheptylamino)methylenebisphosphonic acid and its salts; and 2-hydroxyethylidene-2-(pyridin-3-yl)-1,1-bisphosphonic acid and its sodium salts.

The salts of the above-mentioned bisphosphonic acid derivatives are generally referred to as bisphosphonates.

According to the present invention, it is particularly preferable to use tiludronic acid and its pharmaceutically acceptable salts, especially the disodium salt.

The biological effect of bisphosphonic acid derivatives is to inhibit bone resorption by reducing the activity of the osteoclasts, as indicated in the following publications:

H. Heisch, R. G. G. Russel and M. D. Francis: Diphosphonates inhibit hydroxyapatite dissolution in vitro and bone resorption in tissue culture and in vivo; Science, 1969, 165, 1262–1264;

P. M. Boonekamp, L. J. A. Van der Wee-Pals, M. M. L. Van WijkLennep, C. W. Thesing and O. L. M. Bijvoet: Two modes of action of bisphosphonates on osteoclastic resorption of mineralized matrix; Bone Miner., 1986, 1, 27–39; and A. M. Hanaghan and T. J. Chambers: Dichloromethylene bisphosphonate ($Cl_2$, MBP) inhibits bone resorption through injury to osteoclasts that resorb CIMBP coated bone; Bone Miner., 1989, 6, 33.

Several bisphosphonic acid derivatives are currently being developed on humans or marketed for use in the treatment of bone diseases such as Paget's disease and osteoporosis. These diseases are characterized by an osteoclastic stimulation (more significant in Paget's disease than in osteoporosis), which has to be checked.

An article by H. C. Tennenbaum et al. published in Bone, 1992, 13, 249– 255, refers to an increase in the enzymatic markers of osteogenesis, in vitro, after the administration of low doses of bisphosphonates.

An article by Feretti et al. published in Bone Miner., 1990, 11, 111–122, refers to an improvement in the biomechanical properties of bone, with no increase in the bone mass, observed ex vivo after the administration of bisphosphonates.

Furthermore, as bisphosphonates inhibit bone resorption and as the resorption step is essential in the process of bone repair which takes place following a fracture or bone surgery, the administration of bisphosphonates could not have been expected to have a beneficial effect on bone repair; on the contrary, bisphosphonates might have been expected to be contra indicated in the case of bone repair. F. Bonnel and B. Tachot may thus be cited: Biologie de la cicatrisation osseuse des fractures (Biology of bone healing in fractures)

in Le Tissu Osseux (op. cit.: edited under the guidance of L. Teot, J. Vidal and J. Dossa, collection: Biologic de l'appareil locomoteur, Diffusion Vigot, 1989): "Diphosphonates. They have the effect of checking osteoclastic resorption and on the whole suppress bone remodeling. In cases of fracture, they must be withdrawn until consolidation has taken place".

It has nevertheless been found, totally unexpectedly, that bisphosphonic acid derivatives are useful in bone repair, especially for accelerating it.

Thus the present invention relates to a method of promoting bone repair in human or veterinary medicine which comprises the administration of a therapeutically effective amount of bisphosphonic acid derivatives. Said method is particularly suitable following a fracture or bone surgery. It includes the use of drugs containing at least one bisphosphonic acid derivative.

Such drugs can be used in human medicine and in veterinary medicine.

Such drugs can be administered by different modes of administration, for example orally, parenterally, transdermally or by means of an implant.

When a drug for oral administration is prepared, it is possible to use any suitable excipient and in particular an excipient which facilitates the absorption of the drug, such as sodium laurylsulfate.

The administration doses of the drug according to the invention depend on the bisphosphonic acid derivative used, the mode of administration and the magnitude of the desired effect on bone repair.

The drug administered according to the invention can be administered as a single or repeat dose. For repeat-dose administration, it is possible to choose daily continuous administration, 1 to 3 times a day, throughout the duration of the fracture repair (one to several months), or intermittent administration, for example 1 day a week for one to several months.

The dosage unit can comprise from 0.001 mg to 400 mg of bisphosphonic acid derivative(s) of formula (I), more particularly 0.01 mg to 400 mg.

Thus the administration doses of the drug prepared according to the invention can vary from 0.001 mg to 1.2 g per day, more particularly from 0.01 mg to 1.2 g per day.

The dosage unit preferably comprises from 0.1 to 250 mg of bisphosphonic acid derivative(s) of formula (I).

For oral administration, the pharmaceutical composition according to the invention can be in the form of a tablet, a gelatin capsule, a powder, granules, drops or any other form suitable for oral administration.

The composition administered according to the invention can also contain ingredients normally used in pharmacy for the preparation of oral forms. Thus the composition according to the invention can contain a disintegrant, a flow enhancer, a lubricant and any suitable bulk excipient.

Bulk excipients which can be used are lactose, cellulose or starches. Lubricants which can be used are stearic acid, magnesium stearate, L-leucine or, for example, glycerol tribehenate. Disintegrants which can be used are sodium carboxymethyl starch, crosslinked sodium carboxymethyl cellulose or, for example, crosslinked polyvinylpyrrolidone. Flow enhancers which can be used are pure silica or colloidal silicon dioxide.

The present invention further relates to the administration of instantaneously dissolving oral forms and the effervescent oral forms obtained by adding an effervescent couple to the composition according to the invention. Examples of effervescent couples which can be used are tartaric acid and sodium bicarbonate or citric acid and sodium bicarbonate.

The tablet form is a preferred form according to the invention. The invention further relates to the administration of instantaneously dissolving tablets, effervescent tablets and coated tablets. A composition containing sodium laurylsulfate, according to European patent EP 336851, is particularly suitable.

For oral administration of the tiludronate, the unit dose varies from 0.05 mg to 1000 mg, advantageously from 0.05 mg to 400 mg and more particularly from 0.1 mg to 250 mg.

For oral administration of the pamidronate or etidronate, the unit dose varies from 0.05 mg to 1 g, advantageously from 0.05 mg to 400 mg.

For oral administration of the alendronate, risedronate or (cycloheptylamino)methylenebisphosphonic acid or one of its salts, the daily dose administered varies from 0.001 mg to 100 mg, preferably from 0.01 mg to 100 mg.

Parenteral administration is carded out using aqueous suspensions, isotonic saline solutions or sterile and injectable solutions which can contain compatible pharmacological dispersants and/or wetting agents, for example propylene glycol or butylene glycol.

For transdermal administration, the composition according to the invention can be in the form of a cream, an ointment or a composition for transdermal administration.

EXAMPLE 1: Measurement of Bone Repair

An experimental study of bone repair was performed on dogs using a hemiosteotomy model.

The principle of hemiosteotomy is to produce an incomplete fracture line along the diaphysis of a long bone (ulna) belonging to a double radius. The half-fracture is thus stabilized by the unfractured part of the same bone and by the second bone, avoiding the use of any fixing equipment.

Three groups made up of four male Beagle dogs were used; they were respectively treated once a day by garage for six weeks (D 0 to D 45) after the hemiosteotomy. The products are administered in the form of gelatin capsules.

TABLE 1

| Group | Number of animals | Product | Dose (mg/kg) |
| --- | --- | --- | --- |
| 1 | 4 | vehicle (empty gelatin capsules) | — |
| 2 | 4 | tiludronate | 5 |
| 3 | 4 | etidronate | 10 |

Two administrations of tetracycline were carried out several days apart in order to mark the mineralization line at two different times on days D 26 and D 27 and then D 41 and D 42.

On D 45 after the hemiosteotomy, the animals were sacrificed. The hemiosteotomized bones were removed and fixed for the following histomorphometric examination:

measurement of the number of osteoclasts per $mm^2$;

measurement of the active area of resorption (%): this is the area occupied by osteoclasts relative to the total area; this measurement enables the bone resorption to be evaluated;

measurement of the area of double marking (%) relative to the total area of the bone: this measurement enables the lamellar bone to be quantified; and measurement of the trabecular volume (TV), expressed as a percentage of the total bone volume (BV); at the break created by the hemiosteotomy, this volume represents the amount of bone formed, including the osteoid border and the mineralized tissue.

On day D 45 after the hemiosteotomy, biomechanical tests are also carried out by analysis of the resonant frequency: the resonant frequencies are measured on the ulna in the longitudinal plane, the vibrations are recorded by a microphone placed 1 cm above the bone, and the excitation is performed with a hammer impact halfway along the length of the ulna. The signals are transmitted to a spectral analyzer, which gives the frequency of the spectrum, and the resonance frequencies are determined.

The mean of 4 measurements is calculated for the recorded signals. Two parameters are evaluated in this way:

1) Bone stiffness: evaluation of the resistance of the bone to vibrations in the longitudinal plane.

The calculated stiffness is: $F^2M$ in $Hz^2 \times g$.

F: resonant frequency (Hertz).

M: mass (grams).

2) Buckling strength: calculation of the force opposed to the vibrations in the longitudinal plane.

The buckling strength is $F^2ML$ in $Hz^2 \times g \times mm$.

L: length (mm).

The results (mean and root-mean-square error: r.m.s. error) are shown in the Tables below:

TABLE 2

| Group (product) | Number of osteoclasts per mm² (r.m.s. error) | Active area of resorption (%) (r.m.s. error) | Area of double marking (%) (r.m.s. error) |
| --- | --- | --- | --- |
| Group 1 (control) | 8.19 (1.19) | 3.32 (0.35) | 2.21 (1.48) |
| Group 2 (tiludron-ate) | 9.54 (1.73) | 5.44 (0.61) | 20.55* (2.96) |
| Group 3 (etidronate) | 5.58 (0.92) | 4.95 (0.18) | 6.49 (4.12) |

*p < 0.05

The results clearly show an increase in the amount of definitive lamellar bone for the two bisphosphonates, whereas there was no concurrent modification of the bone resorption parameters.

TABLE 3

| Group (product) | Trabecular bone volume BV/TV % (r.m.s. error) | Bone stiffness $Hz^2 \times g$ (r.m.s. error) | Buckling strength $Hz^2 \times g \times mm$ (r.m.s. error) |
| --- | --- | --- | --- |
| Group 1 (control) | 65.5 (2.6) | 85.9 (16.9) | 101.8 (17.1) |
| Group 2 (tiludron-ate) | 70.4 (0.9) | 157.4 (26.7) | 192.8 (32.5) |
| Group 3 (etidronate) | 60.3 (6.2) | 110.8 (25.9) | 135.4 (34.1) |

These results show that after the treatment with a bisphosphonate:

the trabecular bone volume has not been significantly reduced by the treatment, and the biomechanical properties are improved; in fact, the bone stiffness and the buckling strength are increased, especially with the tiludronate.

EXAMPLE 2: Tablet for Improving Bone Repair

| Divisible tablet: | |
| --- | --- |
| disodium salt of tiludronic acid corresponding to 200 mg of acid | 240 mg |
| sodium laurylsulfate | 4.5 mg |
| crosslinked sodium carboxymethyl cellulose | 24 mg |
| microcrystalline lactose | 177 mg |
| magnesium stearate | 4.5 mg |
| | 450 mg |

EXAMPLE 3: Tablet for Improving Bone Repair

| Divisible tablet: | |
| --- | --- |
| disodium salt of tiludronic acid corresponding to 50 mg of acid | 60 mg |
| sodium laurylsulfate | 3 mg |
| crosslinked sodium carboxymethyl cellulose | 6 mg |
| anhydrous lactose | 44.25 mg |
| magnesium stearate | 1.25 mg |
| | 114.5 mg |

EXAMPLE 4: Tablet for Improving Bone Repair

| disodium salt of tiludronic acid corresponding to 25 mg of acid | 30 mg |
| --- | --- |
| crosslinked sodium carboxymethyl cellulose | 3 mg |
| magnesium stearate | 0.75 mg |
| microcrystalline lactose | 22.25 mg |
| | 56 mg |

EXAMPLE 5: Injectable Solution for Improving Bone Repair

| disodium salt of etidronic acid | 300 mg |
| --- | --- |
| water for injectable preparations | |
| | 6 ml |

EXAMPLE 6: Perfusion Preparation for Improving Bone Repair

| lyophilizate of sodium pamidronate | 15 mg |
| --- | --- |
| water for injectable preparations | 6 ml |

EXAMPLE 7: Perfusion Preparation for Improving Bone Repair

| disodium salt of clodronic acid | 300 mg |
| --- | --- |
| sodium hydroxide    qsp pH 5 | |
| water for injectable preparations | |
| | 5 ml |

What is claimed is:

1. A method of promoting bone repair in a mammal which comprises administering to a mammal in need thereof a therapeutically effective amount of disodium salt of tiludronic acid.

2. A method of promoting bone repair in a mammal which comprises administering to a mammal in need thereof a composition comprising a therapeutically effective amount of disodium salt of tiludronic acid and a physiologically acceptable carrier or excipient.

3. A method according to claim 1 wherein the therapeutically effective amount is administered orally.

4. A method according to claim 1 wherein the therapeutically effective amount is administered transdermally.

5. A method according to claim 2 wherein the composition is administered orally.

6. A method according to claim 2 wherein the composition comprises from 0.001 mg to 400 mg of active ingredient.

7. A method according to claim 2 wherein the composition comprises from 0.1 to 250 mg of active ingredient.

8. A method according to claim 2 wherein the composition further comprises sodium laurylsulfate.

9. A method according to claim 2 wherein the composition for oral administration is in the form of a tablet.

10. A method according to claim 9 wherein the tablet comprises:

about 240 mg of disodium salt of tiludronic acid, corresponding to 200 mg of acid;

about 4.5 mg of sodium laurylsulfate;

about 24 mg of cross-linked sodium carboxymethyl cellulose;

about 177 mg of microcrystalline lactose; and about 4.5 mg of magnesium stearate.

11. A method according to claim 9 wherein the tablet comprises:

about 60 mg of disodium salt of tiludronic acid, corresponding to 50 mg of acid;

about 3 mg of sodium laurylsulfate;

about 6 mg of cross-linked sodium carboxymethyl cellulose;

about 44.25 mg of anhydrous lactose; and about 1.25 mg of magnesium stearate.

12. A method of increasing bone stiffness and buckling strength in a fractured mammalian bone which comprises administering to a mammal in need thereof a composition comprising a therapeutically effective amount of disodium salt of tiludronic acid, and a physiologically acceptable carrier or excipient.

13. A method according to claim 12 wherein the effective amount is from 0.001 mg to 400 mg.

14. A method according to claim 13 wherein the composition is in tablet form for oral administration.

* * * * *